US010723999B2

(12) United States Patent
Perrard et al.

(10) Patent No.: US 10,723,999 B2
(45) Date of Patent: Jul. 28, 2020

(54) PROCESS FOR IMPLEMENTING IN VITRO SPERMATOGENESIS AND ASSOCIATED DEVICE

(71) Applicants: KALLISTEM, Lyons (FR); UNIVERSITÉ CLAUDE BERNARD LYON 1, Villeurbanne (FR); CENTRE NATIONAL DE LA RECHERCHE SCIENTIFIQUE (C.N.R.S), Paris (FR); INSTITUT NATIONAL DE LA RECHERCHE AGRONOMIQUE (INRA), Paris (FR); ECOLE NORMALE SUPERIEURE DE LYON, Lyons (FR)

(72) Inventors: Marie-Hélène Perrard, Craponne (FR); Philippe Durand, Craponne (FR); Laurent David, Lyons (FR)

(73) Assignees: KALLISTEM, Lyons (FR); UNIVERSITÉ CLAUDE BERNARD LYON 1, Villeurbanne (FR); CENTRE NATIONAL DE LA RECHERCHE SCIENTIFIQUE (C.N.R.S.), Paris (FR); INSTITUT NATIONAL DE LA RECHERCHE AGRONOMIQUE (INRA), Paris (FR); ECOLE NORMALE SUPERIEURE DE LYON, Lyons (FR)

( * ) Notice: Subject to any disclaimer, the term of this patent is extended or adjusted under 35 U.S.C. 154(b) by 0 days.

(21) Appl. No.: 15/106,714

(22) PCT Filed: Dec. 19, 2014

(86) PCT No.: PCT/EP2014/078887
§ 371 (c)(1),
(2) Date: Jun. 20, 2016

(87) PCT Pub. No.: WO2015/092030
PCT Pub. Date: Jun. 25, 2015

(65) Prior Publication Data
US 2017/0029768 A1 Feb. 2, 2017

(30) Foreign Application Priority Data
Dec. 20, 2013 (EP) ..................................... 13306813

(51) Int. Cl.
*C12N 5/076* (2010.01)
*C12N 5/075* (2010.01)

(52) U.S. Cl.
CPC .......... *C12N 5/061* (2013.01); *C12N 5/0609* (2013.01); *C12N 2500/05* (2013.01); *C12N 2500/25* (2013.01); *C12N 2500/38* (2013.01); *C12N 2501/31* (2013.01); *C12N 2501/385* (2013.01); *C12N 2501/392* (2013.01); *C12N 2533/72* (2013.01)

(58) Field of Classification Search
None
See application file for complete search history.

(56) References Cited

U.S. PATENT DOCUMENTS

| 8,647,861 B2* | 2/2014 | Ingber | C12N 5/0696 435/283.1 |
| 2003/0027329 A1* | 2/2003 | Lee | C12N 5/061 435/325 |
| 2008/0220524 A1* | 9/2008 | Noll | C12N 5/0068 435/395 |
| 2012/0040463 A1* | 2/2012 | Domard | B01D 69/087 435/400 |
| 2012/0083034 A1* | 4/2012 | Izadyar | C12N 5/0609 435/354 |

FOREIGN PATENT DOCUMENTS

| WO | WO 2005/100551 | 10/2005 |
| WO | WO 2009/047346 | 4/2009 |
| WO | WO 2009/056602 | 5/2009 |
| WO | WO 2011/057128 | 5/2011 |
| WO | WO 2011/140428 | 11/2011 |

OTHER PUBLICATIONS

Perrard, M., Hue, D., Staub, C., Vern. Y. L., Kerboeuf, D., & Durand, P. (2003). Development of the meiotic step in testes of pubertal rats: Comparison between the in vivo situation and under in vitro conditions. *Molecular Reproductions and Development*, 65(1), 86-95. doi:10.1002/mrd/10259.
Wang, D., Li, K., & Teo, W. (2000). Preparation of annular hollow fibre membranes. *Journal of Membrane Science*, 166(1), 31-39. doi:10.1016/s0376-7388(99)00242-2.
Bettahalli, N., Vicente, J., Moroni. L., Higuera. G , Blitterswijk, C. V., Wessling. M., & Stamatialis, D. (2011). Integration of hollow fiber membranes improves nutrient supply in three-dimensional tissue constructs. *Acta Biomaterialia*, 7(9), 3312-3324. doi:10.1016/j.actbio.2011.06.012.
Notice of Reasons for Rejection dated Oct. 30, 2018 in corresponding Japanese Patent Application No. 2016-560038.
International Search Report for PCT/EP2014/078887, dated Feb. 19, 2015.

(Continued)

*Primary Examiner* — Emily A Cordas
(74) *Attorney, Agent, or Firm* — B. Aaron Schulman, Esq.; Stites & Harbison, PLLC

(57) ABSTRACT

The present invention relates to a process for in vitro spermatogenesis from male germinal tissue comprising conducting maturation of testicular tissue comprising germ cells in a bioreactor which is made of a biomaterial and comprises at least one cavity wherein the germinal tissue is placed, and recovering elongated spermatids and/or spermatozoa.

21 Claims, 8 Drawing Sheets

(56) References Cited

OTHER PUBLICATIONS

Notification of Transmittal of the International Search Report and the Written Opinion of the International Searching Authority, or the Declaration for PCT/EP2014/078887 dated Feb. 19, 2015.
J.-B. Stukenborg et al: "New horizons for in vitro spermatogenesis? An update on novel three-dimensional culture systems as tools for meiotic and post-meiotic differentiation of testicular germ cells", Molecular Human Reproduction, vol. 15, No. 9, Jun. 27, 2009 (Jun. 27, 2009), pp. 521-529, XP055106756, ISSN: 1360-9947, DOI: 10.1093/molehr/gap052 abstract.
Takuya Sato et al: "In vitro production of functional sperm in cultured neonatal mouse testes", Nature, vol. 471, No. 7339, Mar. 24, 2011 (Mar. 24, 2011), pp. 504-507, XP055106782, ISSN: 0028-0836, DOI: 10.1038/nature09850 cited in the application abstract.
Sato T et al: "In vitro production of fertile sperm from murine spermatogonial stem cell lines", Nature Communications 2011 Nature Publishing Group GBR, vol. 2, No. 1, 2011, XP009176806, ISSN: 2041-1723 abstract figure 1.
T Miura et al: "Hormonal induction of all stages of spermatogenesis in vitro in the male Japanese eel (*Anguilla japonica*).", Jul. 1, 1991 (Jul. 1, 1991), pp. 5774-5778, XP055106531, Retrieved from the Internet: URL:http://www.ncbi.nlm.nih.gov/pmc/articles/PMC51960/pdf/pnas01063-0305.pdf [retrieved on Mar. 10, 2014] abstract "Organ Culture Techniques"; p. 5774.
N. Cremades et al: "In-vitro maturation of round spermatids using co-culture on Vero cells", Human Reproduction, vol. 14, No. 5, May 1, 1999 (May 1, 1999), pp. 1287-1293, XP055106926, DOI: 10.1093/humrep/14.5.1287 abstract.
Robert E. Chapin et al: "Assuring safety without animal testing: The case for the human testis in vitro", Reproductive Toxicology, vol. 39, Aug. 1, 2013 (Aug. 1, 2013), pp. 63-68, XP055107074, ISSN: 0890-6238, DOI: 10.1016/j.reprotox.2013.04.004 cited in the application p. 66.
J.-B. Stukenborg et al: "Coculture of Spermatogonia With Somatic Cells in a Novel Three-Dimensional Soft-Agar-Culture-System", Journal of Andrology, vol. 29, No. 3, Jan. 9, 2008 (Jan. 9, 2008), pp. 312-329, XP055106934, ISSN: 0196-3635, DOI: 10.2164/jandrol.107.002857 abstract figure 5.
Godet M et al: "Meiotic progression of rat spermatocytes requires mitogen-activated protein kinases of Sertoli cells and close contacts between the germ cells and the Sertoli cells", Developmental Biology, Academic Press, Amsterdam, NL, vol. 315, No. 1, Mar. 1, 2008 (Mar. 1, 2008), pp. 173-188, XP026809482, ISSN: 0012-1606 [retrieved on Jan. 29, 2008] cited in the application abstract.
C Staub: "The Whole Meiotic Process Can Occur in Vitro in Untransformed Rat Spermatogenic Cells", Experimental Cell Research, vol. 260, No. 1, Oct. 10, 2000 (Oct. 10, 2000), pp. 85-95, XP055106177, ISSN: 0014-4827, DOI: 10.1006/excr.2000.4998 abstract.

\* cited by examiner

PROCESS FOR IMPLEMENTING IN VITRO SPERMATOGENESIS AND ASSOCIATED DEVICE

The present invention relates to a process for implementing in vitro spermatogenesis and associated device.

Each year, 160,000 children worldwide are affected by pediatric cancer. Progress during the past 30 years in oncology, of which pediatric cancers were the major beneficiaries, can now achieve cure rates of 75-80% in developed countries. However, only 33% of male children who have survived cancer during childhood produce sperm of normal quality when they are adults. Indeed, cancer therapies are known for their gameto-toxic effects that can cause sterility. While adults can be offered to freeze sperm before starting treatment (for example cancer therapy) to preserve their fertility, it is of course not possible for children. The only currently feasible conservation protocol for these boys is to make a collection and cryopreservation of their testicular tissue. However, today, there is no guarantee that future scientific advances will restore their fertility in the context of a medically assisted parental project.

There is thus a need to develop techniques to preserve the fertility of these children in order to fulfill their future parental project.

In addition to cancer therapies undergone during the childhood or adulthood, sterility can be due to genetical or acquired non-obstrusive azoospermia, bilateral chryptorchidism, severe sickle cell disease, etc.

There is thus a need to provide a process enabling to produce spermatozoa starting from testicular tissue in order to restore fertility.

For several decades, reproductive biologists have been trying to develop a technology to achieve spermatogenesis in vitro (ex vivo) in mammals. Spermatogenesis is a unique complex process involving several stages of cell division and cellular differentiation which leads to the formation of elongated spermatids and spermatozoa. A complete cycle of spermatogenesis takes about 30 days in mice, 54 days in rats and 72 days in human. Spermatogenesis occurs within the seminiferous tubules where the germ cells are in close association with Sertoli cells, the somatic cells needed to achieve this process. The local (intra-testicular) mechanisms regulating spermatogenesis still remain poorly understood. This partly explains why, despite sustained investment in research, no method has now reproduced in vitro (or ex vivo) this entire process in humans. The most significant advances in this field are recent. A Japanese team which has developed a method of organotypic culture has recently announced that they have obtained in vitro fertilizing sperm from spermatogonia of immature mice (Takuya Sato et al., Nature, 2011, 471, 504-508). While the identification of culture conditions that permit immature male germ cells to mature into functional sperm is a major breakthrough, there are still several issues that require attention. Not surprisingly, efficiency is a major concern. Only the peripheral region of testes fragments exhibited advanced spermatogenesis in their system, while the center lost normal morphology and had large numbers of degenerating cells after 40 days of culture. Far fewer elongated spermatids and spermatozoa are produced per input immature male germ cell using the currently available in vitro system than in a normal testis in vivo. Flagellated sperm were observed in only 5 out of 11 cultured explants from neonatal testes 2 and in only 3 out of 17 cultured explants from SSC transplanted testes (Sato et al., Nat Commun., 2011, 2, 472). More recently, a German-Israeli team used a co-culture of isolated testicular cells in 3D culture. However, they did not report on the ability of the spermatozoa obtained to produce offsprings. In addition, these techniques have drawbacks related to their implementation complexity and the large amount of biological tissue they require and seem hardly conductive to adaptation in humans.

It is also known from Staub et al (Experimental Cell Research, 2000, 260, 85-95), Godet et al (Developmental Biology, 2008, 315, 173-188) and Perrard et al (Molecular Reproduction and Development, 2003, 65, 86-95) the use of a bicameral chamber for implementing spermatogenesis. However, these methods do not enable to obtain fertilizing spermatids or spermatozoa which are fertilizing.

Hollow fibers made of a coagulated polysaccharide hydrogel, such as based on chitosan, have been described and proposed as bioreactor that may be used in tissue engineering, biological membranes or slow-release vector. Hydrogels are macromolecular networks, preferably 3D elastic macromolecular netwaorks, with high water content, so that they can mimic hydrated native tissues. N. M. S. Bettahalli et al. (Acta Biomaterialia 7, 2011, 3312-3324) discloses the use of hollow fiber membranes to improve nutrient supply in three-dimensional tissue constructs in the field of tissue-engineered constructs based on scaffolds combined with cells or biological molecules for the treatment of tissue defects. Wang et al., Membr. Sci. 2000, 166, 31-39 disclose annular hollow fibers. WO2009/044053 discloses mono- or multi-membrane hollow fibers made of a coagulated polysaccharide hydrogel, such as based on chitosan. Robert E. Chapin and Kim Boekelheide (Reproductive Toxicology 39, 2013, 63-68) interested in the creation of in vitro models of tissues using human cells in the field of spermatogenesis and suggested that evaluation should be done of testis cells in some new hydrogels and/or 3D matrices that might support the development of multicompartments. They suggested that the presence of Sertoli cells and germ cells should be key to the in vitro reconstruction of the testis tissue.

There is still a need to provide a process to implement in vitro spermatogenesis for human and animals.

The objective of the present invention is to provide a process of in vitro spermatogenesis to obtain fertilizing elongated spermatids or spermatozoa which are fertilizing.

Another objective of the present invention is to provide such a process which is efficient even based on small amounts of germinal tissue.

Another objective of the present invention is to provide a process of in vitro fertilization. Other objectives will appear by reading the description below.

The above mentioned problems and prior art drawbacks are surprisingly solved by the present invention which relates to a process for in vitro (ex vivo) spermatogenesis from male germinal tissue comprising conducting maturation of said germinal tissue in a bioreactor which is made of a biomaterial and comprises at least one cavity wherein the germinal tissue is placed. At the end of the maturation process or a maturation time, elongated spermatids and/or spermatozoa are recovered.

According to the present invention "biomaterial" should be understood as a biocompatible material, i.e. a material that is not toxic for cells or tissue.

The present invention is based on the finding that male germinal tissue is to be used and confined in a 3D biocompatible structure. The germinal tissue is a testicular tissue comprising germ cells. It is more preferably seminiferous tubules or fragment(s) of seminiferous tubules. It is generally more convenient to manipulate fragments of tubules, and it is advantageous to mix fragments of several different tubules in order to have cells (germ cells and/or Sertoli cells) at different stages. It may also be of interest to add to the tubules or fragments, germ cells or other seminiferous cells, recovered from seminiferous tubules or their fragments. The tubules are dissociated or separated from the remaining testicular tissue, in particular from the surrounding tissue or Leydig cells, for example by mechanical or chemical treatment.

The present invention thus relates to a process for in vitro spermatogenesis from male germinal tissue comprising conducting maturation of testicular tissue comprising germ cells in a bioreactor which is made of a biomaterial and comprises at least one cavity wherein the germinal tissue is placed, and recovering elongated spermatids and/or spermatozoa.

According to the invention, the testicular tissue comprises at least one seminiferous tubule or fragments of at least one seminiferous tubule, preferably several seminiferous tubules or fragments of several seminiferous tubules, more preferably fragments from 2, 3, 4, preferably 5, to 10, 20, 30, 40 or 50 seminiferous tubules (every combinations are encompassed). For example, the testicular tissue comprises fragments from 2 to 50, 3 to 40, 4 to 30, 5 to 20 seminiferous tubules. These tubules may come from testis from the same patient or donor, or from different donors.

The seminiferous tubules may be separated from the testis through methods known to the person skilled in the art. It may be a mechanical or enzymatic separation of the tubules with respect to the remaining testis and the Leydig cells, for example using collagenase and separation. It may be mechanical separation, for example using a scalpel and the like. "Fragments" means in the sense of the invention portions of the seminiferous tubules. The fragments of seminiferous tubules may have a size facilitating the manipulation thereof and their placing into the cavity. Typically, their size is comprised between about 1 and about 5 mm, this being the length of tubule portion. The fragments, as the original tubules, preferably comprise germ cells, Sertoli cells and peritubular cells (especially of myoid type), typically in or close to the native configuration within intact tubules. The testis may be from a patient or from one or several donors. In the process of the present invention, the germinal tissue is from a patient which can be a human or a non-human. Preferably, the patient is a human or a non-human mammal.

According to the invention, the testicular tissue comprises germ cells, Sertoli cells and peritubular cells. Leydig cells may also be present.

According to the invention, cells selected from the group consisting of germ cells, Sertoli cells, peritubular cells and mixtures thereof, are added to the testicular tissue.

Preferably, the germinal tissue can be either:
a) a sample of the patient comprising seminiferous tubules, or fragments of seminiferous tubules, comprising germ cells; Sertoli cells; peritubular cells (especially of myoid type); and possibly Leydig cells; or
b) seminiferous tubules or fragments of seminiferous tubules comprising germ cells obtained from the patient and admix with at least Sertoli cells; peritubular cells (especially of myoid type); and possibly Leydig cells of one or more donors.

In addition to a) and b) it is also possible to add germ cells and/or Sertoli cells recovered from seminiferous tubules or their fragments, the tubules may have been dissociated for example by mechanical or chemical treatment and further treated to recover the germ cells and/or the Sertoli cells.

The male germinal tissue can be from a prepubertal or postpubertal patient. For example it can be from:
A healthy prepubertal or postpubertal patient about to undergo a gonado-toxic treatment or surgery, for example cancer-therapy;
A postpubertal patient having germinal tissue but who does not produce spermatozoa for example due to genetic or acquired non-obstrusive azoospermia, bilateral chryptorchidism during childhood or severe sickle cell disease;
A prepubertal patient having bilateral chryptorchidism or severe sickle cell disease;
Endangered species;
Horses, camel, dromedary or pets which will be submitted to a medical or surgical treatment, such as castration;
livestock.

Preferably, the germinal tissue is from:
A healthy prepubertal or postpubertal human or animal about to undergo a gonado-toxic treatment or surgery, for example cancer therapy;
A postpubertal human or animal who does not produce spermatozoa for example due to genetic or acquired non-obstrusive azoospermia, bilateral chryptorchidism during childhood or severe sickle cell disease;
A prepubertal human having bilateral chryptorchidism or severe sickle cell disease.

The bioreactor of the present invention is made of a biomaterial and comprises at least one cavity wherein the germinal tissue is placed or confined. According to the present invention it should be understood by "a bioreactor comprises at least one cavity wherein the germinal tissue is placed or confined" that the bioreactor is either pre-constituted and comprises a cavity wherein the germinal tissue is introduced or the bioreactor is formed around the germinal tissue, the germinal tissue being thus comprised in a cavity which is formed around it during the formation of the bioreactor. Accordingly, it should be understood that the expression "place (or introduce or fill) the germinal tissue into at least one cavity of the bioreactor" means placing the germinal tissue into at least one cavity of a bioreactor or forming a bioreactor around the germinal tissue in order to confine it. Typically, the cavity is filled or substantially filled with the germinal tissue. Typically, the germinal tissue is confined or substantially confined in the cavity. Advantageously, the confinement will be maintained until the end of the maturation. If needed, fragments of biomaterial may be introduced into the channel along with the germinal tissue in order to help the confinement effect. According to a feature, the cavity is closed or sealed during the maturation process.

Advantageously, the germinal tissue is confined in the cavity which enables to maintain a 3-dimensional structure close to the in vivo structure of the seminiferous tubules. When seminiferous tubules or fragments thereof are used as germinal tissue (as mentioned below), the confinement allows to keep their structure along the maturation process. On the contrary, the actual devices for general cell maturation or the suggested methods based on isolated cells do not enable to match the in vivo architecture into seminiferous tubules and the cell maturation cannot be conducted until term.

Advantageously, the bioreactor is relatively flexible and thus enables growth of the seminiferous tubules during the spermatogenesis process, on the contrary to existing device which are more rigid. This is due to the material used for the bioreactor.

The volume of the cavity is depending on the amount of germinal tissue that is used. Also, as explained herein, it is possible to add material, such as biomaterial, to help confinement inside the cavity. Typically, the volume of the cavity may go from about 1 to about 150 mm$^3$, preferably from about 0.5 to about 100 mm$^3$, for example from about 1 to about 30 mm$^3$.

In an embodiment, the bioreactor comprises a pre-formed channel (or a compartment in the form of a channel), it is for example a tubular bioreactor or a tube or hollow fiber made of a biomaterial, e.g. as known in the art. The diameter of the channel is thus suited to the amount and/or size of the germinal tissue in order that the germinal tissue can be placed and confined into the channel in accordance with the inventive concept. In other words, the volume of the channel is adapted to the quantity of germinal tissue introduced in order that the germinal tissue is confined in the channel. The skilled person is able to adapt the volume of the channel by modifying the diameter and/or the length of the channel. This diameter can be determined by the skilled person and is typically from about 100 µm to about 5 mm, preferably from about 1 mm to about 4 mm. Typically, the length of the bioreactor is from about 0.3 to about 5 cm, preferably from about 0.5 to about 3 cm. The germinal tissue is thus placed inside the channel.

In an embodiment, a hardening (e.g. coagulable, cross-linkable, reticulable, etc.) solution or material is placed around the germinal tissue and allowed to harden. The amount of material formed around the germinal tissue and its nature is suited to confine the germinal tissue, and the tissue confinement may be helped by an additional solid structure that may be used at the time of hardening or even it may be maintained to help keeping the structure during maturation (net, grid, walls, mold, container such as Petri dish, tube, . . . ).

Preferably and advantageously, the biomaterial is an hydrogel. Hydrogels are macromolecular, preferably elastic, networks with high water content and they are able to mimic the extracellular matrix of hydrated native tissues. According to the invention "hydrogel" means a viscoelastic mass comprising at least 80%, preferably at least 90% by weight of water, for example between 94 and 99% by weight of water, for example from 96 to 98.5% by weight of water. The hydrogel of the present invention is a chemical hydrogel (interactions responsible of the inter-chain cross-linking are of covalent bond type) or a physical hydrogel (interactions responsible of the inter-chain cross-linking are of physical type for example hydrogen bonds and/or hydrophobic interactions, electrostatic interactions, cristalites or nanocristalites physical crosslinking). Preferably, the hydrogel of the present invention is a physical hydrogel, in order to avoid the toxicity of covalent crosslinker. Preferably, the hydrogel of the invention does not contain any chemical (covalent) or physical (electrostatic) crosslinkers.

Preferably, the bioreactor is in a biomaterial having an effective permeability, (porosity and/or diffusion) relative to the structure and microstructure of the biomaterial, especially related to the porosity of the biomaterial, to the culture medium used for the maturation, to air ($O_2$ and $N_2$) and carbon dioxide. In one embodiment, the cavity is closed during the maturation process. For example, if a tube is used, extremities thereof are sealed. In another embodiment, the bioreactor is closed with a biomaterial permeable to the culture medium used for the maturation, to air and carbon dioxide, for example with a sheet of a biomaterial permeable to the culture medium used for the maturation, to air and carbon dioxide.

The biomaterial according to the invention can be a natural biomaterial or a synthetic biomaterial.

For example, the biomaterial comprises polysaccharides, preferably natural polysaccharides, including modified, especially chemically modified, or hybrid polysaccharide, or structural protein for example keratin or collagen, preferably collagen, or a mixture thereof. Preferably, the biomaterial comprises polysaccharides, preferably natural polysaccharides, including modified, especially chemically modified polysaccharide, or collagen, or a mixture thereof. "Comprises polysaccharides or collagen" means that the biomaterial may comprise at least one polysaccharide or collagen which is the raw compound at the basis of the hydrogel. The biomaterial will also contain ingredients required to produce the hydrogel, such as coagulant, water and the like, and other ingredients. It can be said that the biomaterial is or is made of or is based on the polysaccharide or the structural protein, preferably collagen.

Preferably, the biomaterial comprises a natural polysaccharide, especially chosen among chitosan, hyaluronic acids, alginates, pectines and modified natural polysaccharides such as carboxymethylcellulose (CMC), alone or in mixture. By way of example, the biomaterial comprises chitosan or alginates, alone or in mixture, e.g. chitosan.

Generally said chitosan has an acetylation degree that is suited to confer stability to the bioreactor at least for the duration of one spermatogenesis process, and this degree may be from 0 to 50%. It should be underlined that the more the acetylation degree increases the lower are the mechanical properties of the biomaterial. In order to keep the structure over the whole maturation process, it is preferred to select low or mid acetylation degree, typically from 0 to 30%, preferably from 0 to 15%. More preferably, the acetylation degree is from 0 to 5%. Preferably, the chitosan has a molar mass of the order of 500,000 g/mol.

Preferably, the concentration of polysaccharide or collagen, e.g. chitosan, in the biomaterial, and preferably in the hydrogel, is from 1 to 20%, preferably from 1 to 6%, for example from 1.5 to 4% by weight with respect to the weight of hydrogel.

Advantageously, the biomaterial, and especially its internal structure or microstructure, is such that it enables especially air, carbon dioxide, and the elements of the culture medium into which the bioreactor is placed for maturation, to diffuse through it, especially in order for air, carbon dioxide, and the elements of the culture medium to diffuse through it and reach the germinal tissue or the vicinity of the germinal tissue. Preferably, the thickness of the biomaterial around the cavity has to enable the diffusion of the different elements cited above and thus depend on the biomaterial, especially the biomaterial type and its microstructure. Preferably, the thickness of the biomaterial is from about 0.1 to about 10 mm, preferably from about 0.1 to about 5 mm, preferably from about 0.5 to about 2 mm.

Preferably, the bioreactor is made of a biomaterial comprising a cavity, that is to say that there is a cavity in the biomaterial into which the germinal tissue is placed and confined.

Preferably, the bioreactor is in the form of a hollow fiber, preferably a hollow macrofiber. An example of suitable hollow fibers and method of preparation is described in WO2009044053. The person skilled in the art may refer to this document.

As mentioned herein, in the process according to the invention, the germinal tissue may be introduced into at least one channel or cavity of the bioreactor. Preferably, the channel is then closed at both ends or at the open end. For example, with a hollow fiber, a ligature may be done at both ends or at an open end or as mentioned above a permeable biomaterial can be used, preferably, a ligature may be done at both ends or at an open end.

Advantageously, the process of the present invention does not require large amounts of germinal tissue compared to the method previously implemented (Sato et al., Nat Commun., 2011, 2, 472). Preferably, the amount of germinal tissue introduced into the bioreactor is from about 1 to about 150 mm$^3$, preferably from about 0.5 to about 100 mm$^3$, for example from about 1 to about 30 mm$^3$. This is advantageous, because it is possible to produce elongated spermatids or spermatozoa from a reduced amount of germ cells. This renders the process useful for patients having very few germ cells. As mentioned above the volume of the channel is adapted to the volume of germinal tissue introduced.

Advantageously, before introduction of the germinal tissue in the bioreactor, said bioreactor is incubated with a culture medium.

The bioreactor may be sealed at both ends in order to prevent leakage of the germinal tissue from the channel and placed in a culture medium for maturation into elongated spermatids or spermatozoa.

In accordance with the invention and its various embodiments, a culture medium is used. The composition of the culture medium can be determined by the skilled person based on its general knowledge. Preferably, the culture medium comprises growth factors, hormones, vitamins, antibiotics metabolites, etc., alone or in mixture. For example the hormones can be chosen among insulin, testosterone, FSH (for example ovine/human FSH) alone or in mixture. For example the vitamins are chosen among vitamin C, vitamin E, vitamin A (retinoic acid, retinol), alone or in mixture. For example, the metabolites can be chosen among transferin, pyruvate, alone or in mixture.

Preferably, testosterone is added in the culture medium during the course of the process. The amount of testosterone added is preferably from about $10^{-5}$ to about $10^{-5}$M.

Preferably, the bioreactor containing the germinal tissue is placed in a tank comprising the culture medium. The bioreactor can be immersed in the culture medium or placed at the interface between the air and the culture medium. Preferably, the bioreactor is placed at the interface between the air and the culture medium.

In an embodiment, when the bioreactor is immersed in the culture medium, a bubbling of air is implemented in order to have a sufficient oxygenation for the maturation.

In another embodiment, the bioreactor is placed at the interface between the air and the culture medium. This can be done by any method known by the skilled person and for example by adding in the tank comprising the culture medium a support, preferably a perforated support and the like, such as a grid, at the interface between the air and said culture medium. This advantageously improves the oxygenation and consequently the maturation and the efficiency of the process according to the invention.

As mentioned above, advantageously, the bioreactor has a permeability enabling exchanges between the culture medium and the channel comprising the germinal tissue which enables a contact between the germinal tissue and the culture medium.

The process of the present invention is carried out in temperature condition known by the skilled person to enable maturation of germinal tissue and for example at temperature comprised between about 30 and about 37° C.

According to one aspect, the invention relates to a process for in vitro (ex vivo) spermatogenesis comprising the following steps:

a) Providing a sample of germinal tissue;
b) Providing a bioreactor which is made of a biomaterial and comprises at least one cavity according to the invention, and introducing said germinal tissue into the at least one cavity of said bioreactor; optionally sealing the bioreactor; or forming the bioreactor around the germinal tissue;
c) Placing said bioreactor containing said germinal tissue in a tank comprising a culture medium, especially as defined above;
d) Conducting maturation of the germinal tissue until elongated spermatids and/or spermatozoa are produced;
e) Recovering elongated spermatids and/or spermatozoa from the bioreactor.

Preferably, step f) is implemented as follow:
opening of the bioreactor;
micromanipulation to recover one or more spermatozoa and/or elongated spermatids.

Preferably, the invention relates to a process for in vitro (ex vivo) spermatogenesis comprising the following steps:

a) Providing a sample of germinal tissue;
b) Providing a bioreactor comprising at least one hollow fiber made of an hydrogel material, especially of a polysaccharide or collagen preferably in the physical hydrogel state; and
c) Introducing the germinal tissue into the center channel of the hollow fiber; optionally sealing the hollow fiber;
d) Placing the hollow fiber containing the germinal tissue in a tank comprising a culture medium;
e) Conducting maturation of the germinal tissue until elongated spermatids and/or spermatozoa are produced;
f) Recovering elongated spermatids and/or spermatozoa from the hollow fiber.

In one embodiment, the bioreactor (or the hollow fiber) is immersed in the culture medium, a bubbling of air has to be implemented in order to have a sufficient oxygenation for the maturation.

In another embodiment, the bioreactor (or the hollow fiber) is placed at the interface between the air and the culture medium. This can be done by any method known by the skilled person and for example by adding in the tank comprising the culture medium a support at the interface between the air and said culture medium. This advantageously improves the oxygenation and consequently the maturation and the efficiency of the process according to the invention.

In one embodiment of the process of the invention, the culture medium comprises growth factors, hormones, vitamins, antibiotics metabolites, etc., alone or in mixture. For example the hormones can be chosen among insulin, testosterone, FSH (for example ovine/human FSH) alone or in mixture. For example the vitamins are chosen among vitamin C, vitamin E, vitamin A (retinoic acid, retinol), alone or in mixture. For example, the metabolites can be chosen among transferin, pyruvate, alone or in mixture.

In another embodiment, the culture medium comprises growth factors, hormones, vitamins, antibiotics metabolites, etc., alone or in mixture. For example the hormones can be chosen among insulin, FSH (for example ovine/human FSH) alone or in mixture. For example the vitamins are chosen among vitamin C, vitamin E, vitamin A (retinoic acid, retinol), alone or in mixture. For example, the metabolites can be chosen among transferin, pyruvate, alone or in mixture. The testosterone is then added in the course of the process. Advantageously, at the end of a first wave of maturation, there is still round spermatids in the germinal tissue, and the process can be implemented at least one time more.

In one embodiment, the recovered elongated spermatids and/or spermatozoa are cryopreserved for future medically assisted parental project.

The germinal tissue in the process of the invention can be a fresh or cryopreserved germinal tissue fragment previously obtained from a patient.

The process of the present invention can also be understood as being a treatment for the infertility and/or as a process for preserving fertility. The process of the invention can also be understood as a process for medically assisted procreation.

The present invention also relates to a process of in vitro fertilization comprising the following steps:
  a) Preparation of elongated spermatids and/or spermatozoids according to the process described above; or providing elongated spermatids and/or spermatozoa prepared using this process;
  b) Fertilization of an oocyte with the elongated spermatids and/or spermatozoa from step a).

The present invention also relates to the use of a bioreactor made of a biomaterial and comprising at least one cavity for conducing in vitro spermatogenesis, preferably for the production of elongated spermatids and/or spermatozoa.

Preferably, the bioreactor is as defined above and is preferably a hollow fiber, preferably a hollow macrofiber, as described above.

The present invention also relates to a bioreactor made of a biomaterial and comprising at least one channel or cavity, as described above, and, within this cavity or channel, a germinal tissue as defined herein. As an example, the present invention relates to a hollow fiber comprising in its center channel a germinal tissue. The bioreactor may be an hydrogel, as defined herein.

The present invention also relates to a bioreactor made of a biomaterial and comprising at least one channel or cavity, as described above, comprising in the channel or cavity elongated spermatids and/or spermatozoa. As an example, the invention also relates to hollow fiber, as described above, comprising in its center channel elongated spermatids and/or spermatozoa.

The present invention also relates to a kit for implementing in vitro spermatogenesis from male germinal tissue comprising a bioreactor which is made of a biomaterial and comprises at least one cavity wherein germinal tissue is placed. The bioreactor, the biomaterial, the cavity and the germinal tissue having the above mentioned definitions.

The present invention will now be described by means of examples.

FIGS. 5 and 6 represent testis cross sections of a 8-day and a 60-day-old rat respectively.

PATIENTS

Figure 1:
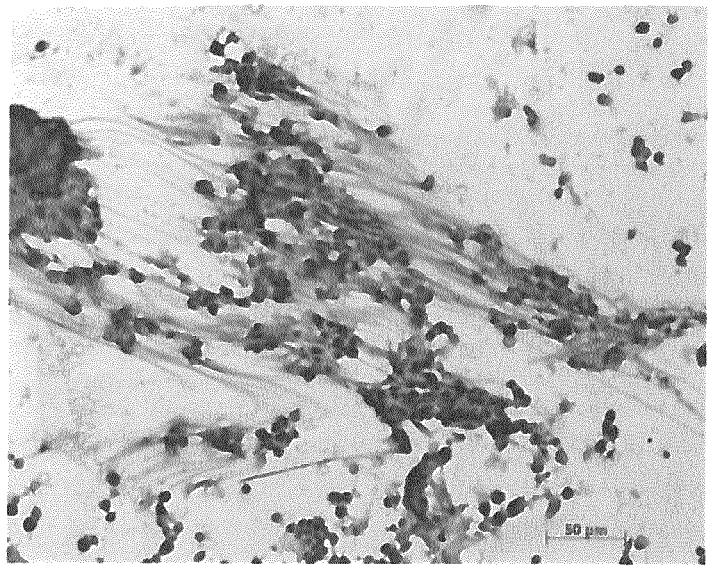
FIGS. 1, 2, 9 and 10 represent germ cells of 20-days old rats after 39 days of culture.

The process according to the invention was implemented on 8 or 20-days-old male Sprague-Dawley rats, on two 1.5-year-old cynomolgus monkey and on a transsexual man.

After anesthesia, rats were killed by decapitation and their testes were quickly removed. Testes of the cynomolgus monkeys and testes of the transsexual man were obtained by surgery. The testes were immersed in Ham's F-12/Dulbecco's Modified Eagle's medium (F12/DMEM, 1:1).

Preparation of Seminiferous Tubules

The tunica albuginea of testes was mechanically removed, and seminiferous tubules were isolated by digestion at 33° C. in F12/DMEM (1:1) containing collagenase, 2 mg/ml lima bean trypsin inhibitor, and 10 mg/ml DNase for 10 min under gentle agitation. Seminiferous tubules were harvested by low-speed centrifugation, washed twice with F12/DMEM (1:1).

Example General Preparation of a Bioreactor:

A solution of a biomaterial, for example chitosan, was prepared in deionized water. This can be operated in a closed reactor with mechanical stirring. After polymer dissolution, the solution is placed in a syringe and the bubbles can be removed by centrifugation (5000 g, 10 min). The solution was extruded using a syringe pump, the syringe is connected to an extrusion cone with extrusion hole diameter of 3 mm. The extrusion is operated in a coagulation bath (NaOH aqueous solution with concentration 1M) inducing the formation of a physical hydrogel, preferably a physical chitosan hydrogel. An external membrane with tubular form is obtained by NaOH radial diffusion from the periphery to the center of the cylindrical extrudate. Depending on the coagulation time (ex: 2 minutes), the thickness of the coagulated hydrogel tube can be adapted to the desired value (ex: 1 mm). After a given coagulation time, the tubular hydrogel still containing a polymer, for example chitosan solution is poured in a large volume of deionized water in order to stop gelation. The non-gelated internal solution can be removed by the introduction of a water or air flux inside the tube thus creating the lumen of the tube, with a length of 1 to 100 cm. The bioreactors can then be cut from this preformed tube at the desired length (about 3 cm). The bioreactors can then be washed in a distilled water baths, and sterilized in water by autoclave treatment (121° C., 20 minutes).

Preparation of the Bioreactor Used for the Examples:

The bioreactors are mono-membrane hollow fibers of chitosan obtained by the process described in WO2009044053. The bioreactor is based on chitosan from squid pen chitin (Mahtani chitosan, Veraval, India; Mahtani batch indexes 114) with acetylation degree of 4% (as determined by Hirai method as described in WO2009044053) with mean molecular mass Mw of 550 kg/mol (as determined by Size exclusion chromatography coupled with refraction index measurement and multi angle light scattering as described in WO2009044053), the interior of the channel obtained has a volume of 20 to 50 $mm^3$.

An acetate chitosan solution, with polymer concentration of 2% w/w in deionized water is prepared with stoichiometric amount of acetic acid with respect to the amine moieties of chitosan. This can be operated in a closed reactor with mechanical stirring. After polymer dissolution, the solution is placed in a syringe and the bubbles can be removed by centrifugation (5000 g, 10 min).

Spermatogenesis 20 to 50 $mm^3$ of the seminiferous tubules were introduced into chitosan tubes. The chitosan tubes were then sealed at both ends and then deposited in a conventional culture well containing approximately 8 ml of culture medium. The medium was changed every two days. The culture medium consisted of 15 mM Hepes-buffered F12/DMEM supplemented with antibiotics, 1.2 g/L $NaHCO_3$, 10 µg/ml insulin, 10 µg/ml transferrin, $10^{-4}$ M vitamin C, 10 µg/ml vitamin E, $3.3 \times 10^{-7}$ M retinoic acid, $3.3 \times 10$-7 M retinol, $10^{-3}$ M pyruvate (all from Sigma), $10^{-7}$M testosterone, and 50 ng/ml porcine FSH. For 8 days old rats, 1.5 year-old cynomolgus monkeys and the transsexual man, testosterone was added to the culture medium after several days of culture.

Histological Studies

At selected days of culture, seminiferous tubules were extruded from the chitosan tubes, were crushed between two microscopic glass slides. Then the nuclei were stained by Harris's hematoxylin solution.

The results of the process implemented are presented in the figures.

Results on 20-Days-Old Rats

In 20-days-old rats, at the beginning of the culture, the most differenciated germ cells were Pachytene spermatocytes (stage X).

Figure 2:
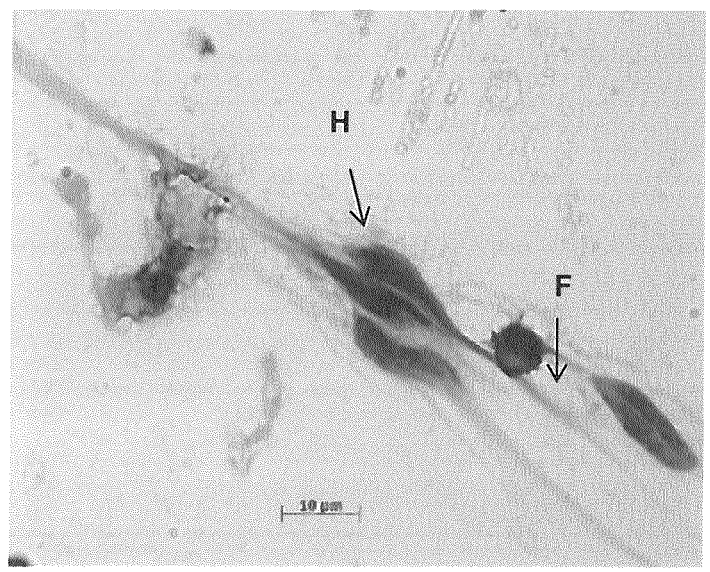

At different days of culture, germ cells were observed. Cells had a similar appearance to their appearance in vivo. Round spermatids (step 1-4 of spermiogenesis) and elongated spermatids (step 9 of spermiogenesis) were visualized on day 11 of culture. After 39 days of culture a cluster of elongated spermatids with their flagella was observed (FIG. 1). It is also observed heads (H in FIG. 2) and flagella (F in FIG. 2) of elongated spermatids (ES) (step 15-17 of spermiogenesis) at a higher magnification (FIG. 2).

Figure 9:
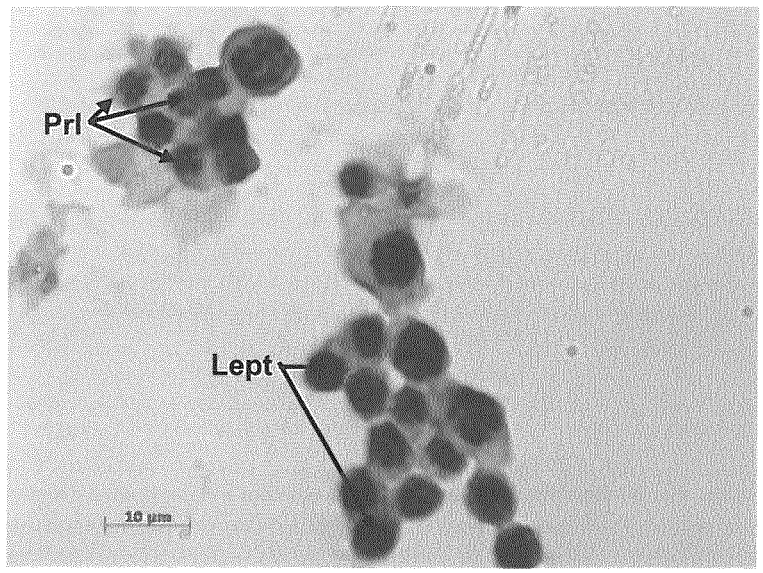
Figure 10:
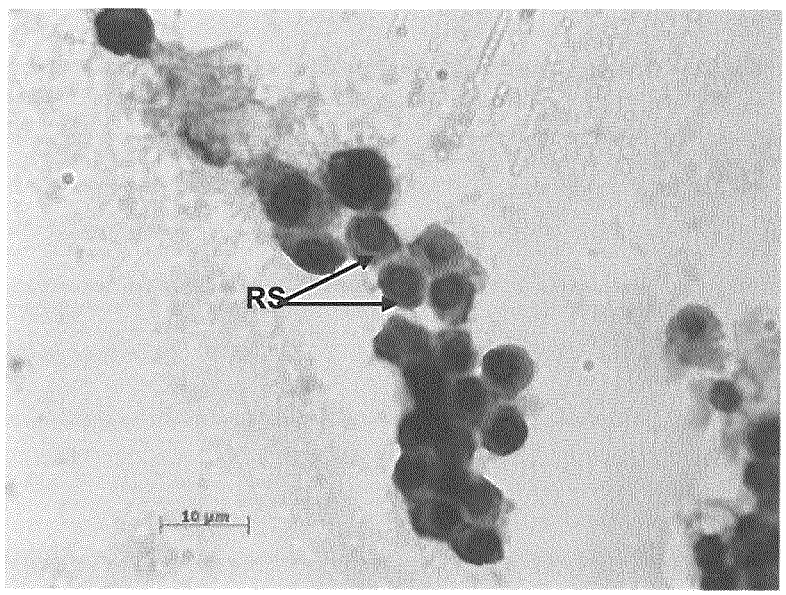

A large cell cluster was observed at day 39 (FIGS. 9 and 10): early meiotic cells, Preleptotene (Prl) and Leptotene (Lept) spermatocytes were still abundant and a new wave of round spermatids (RS) with young Pachytene spermatocytes was present.

Results on 8-Days-Old Rats

By analogy with prebubertal boys who have only spermatogonia in their testes, semiferous tubule cultures from 8 days old rats were performed. Indeed, 8-days-old rats have only spermatogonia in their testes.

After 61 days of culture, cells are obtained after spreading the crushed cultured seminiferous tubules.

Figure 3:
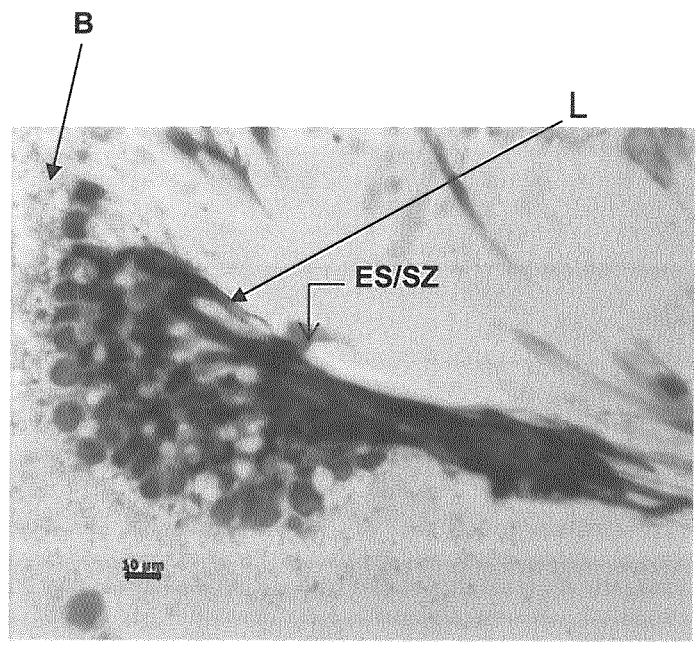
FIGS. 3, 4, 5, 6, 7 and 8 represent germ cells of 8-days old rats after 61 days of culture.

FIG. 3 shows a portion of a seminiferous epithelium with cell associations from the basement (B) of the tubule to the lumen (L). A cluster of elongated spermatids/spermatozoa (ES/SZ in FIG. 3) with their flagella in the lumen of the cultured seminiferous tubules were observed.

Figure 4:
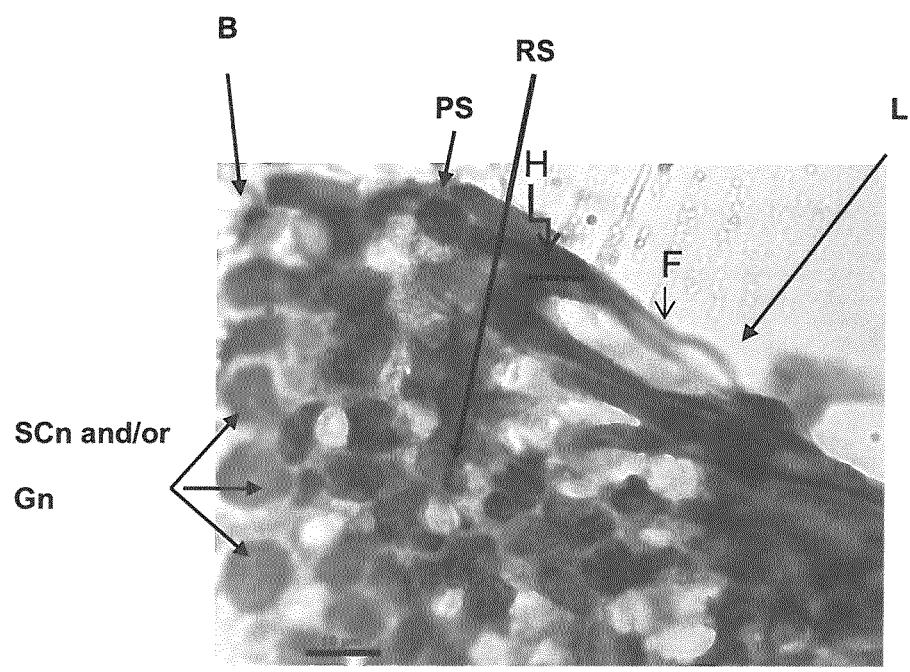
Figure 5:
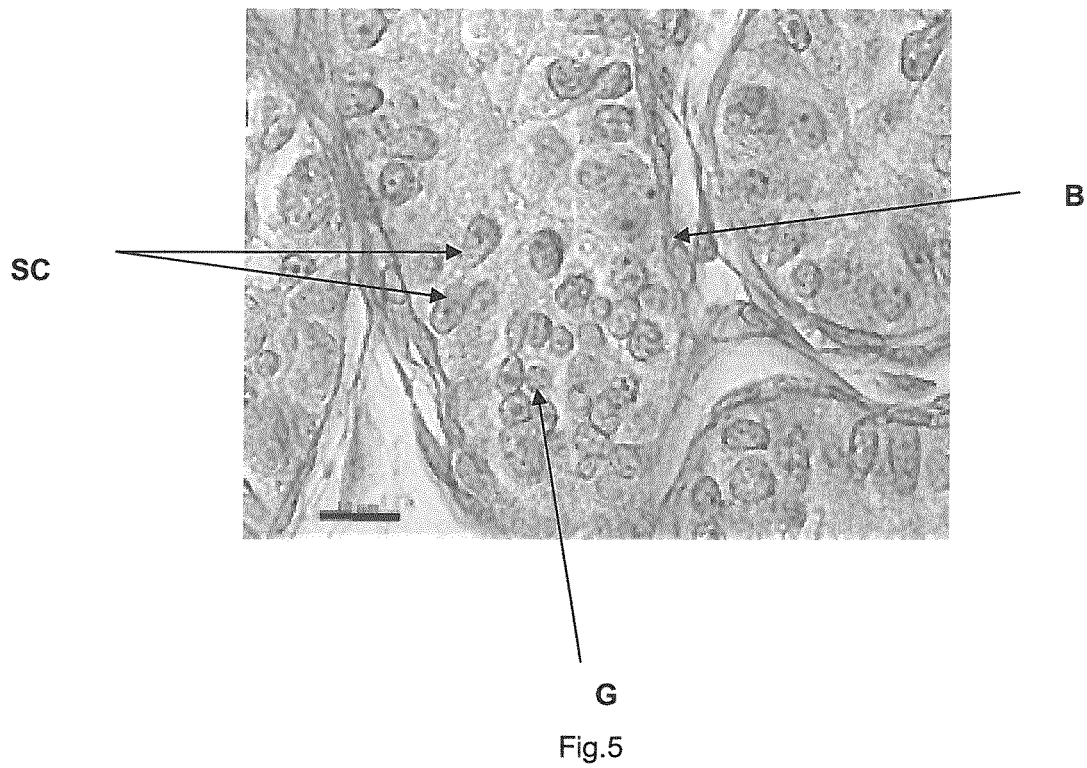

The organization of cells within the bounds of the seminiferous epithelium is seen in FIG. 4. Sertoli cell nuclei (SCn) and/or spermatogonia nuclei (Gn), Pachytene spermatocytes (PS), round spermatids (RS) and ES/SZ were identified at successively higher levels within the epithelium from the basement (B) to the lumen (L) of the seminiferous tubule. Note that no Preleptotene spermatocyte was present. Heads (H) and flagella (F) of ES/SZ were observed (FIG. 4). These results show a growth of cultured seminiferous tubules during the 61 days of culture compared to in vivo 8-day-old rat seminiferous tubules which have no lumen (FIG. 5 shows a cross section of a 8-day-old rat testis). FIG. 5 shows Sertolli cell (SC), the basement of the seminiferous tubules (B) and the cluster of spermatogonia (G).

Figure 6:
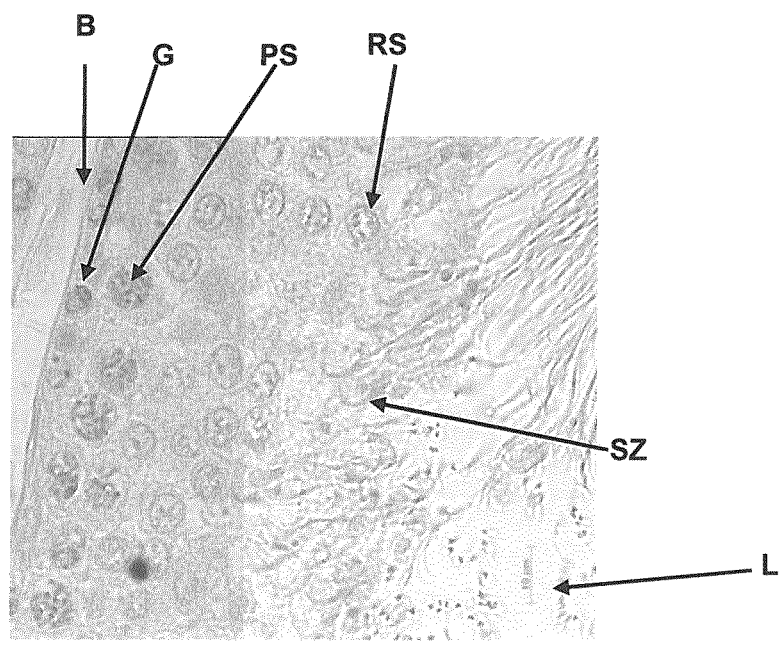

The size of the 61 days cultured seminiferous tubules (FIG. 4) was slightly smaller than the size of in vivo 60-day-old rat seminiferous tubules (FIG. 6 shows a cross section of a 60-day-old rat testis with the basement (B) and lumen (L) of the seminiferous tubules, Spermatogona (G) Pachytene spermatocytes (PS), round spermatids (RS) and spermatozoa (SZ).

Figure 7:
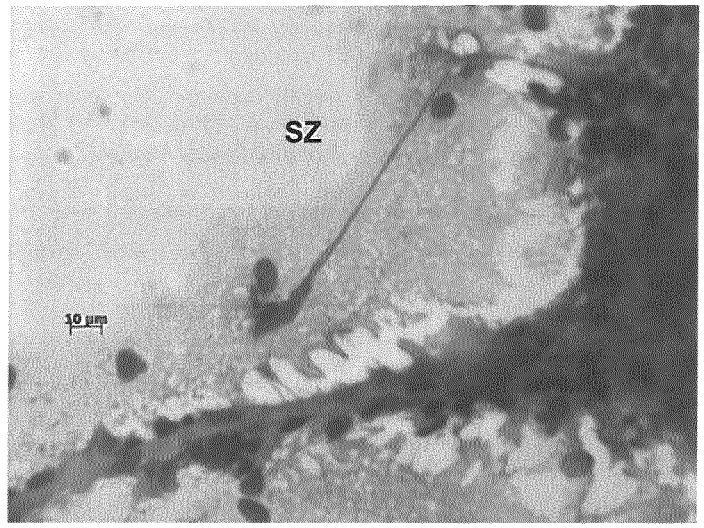
Figure 8:
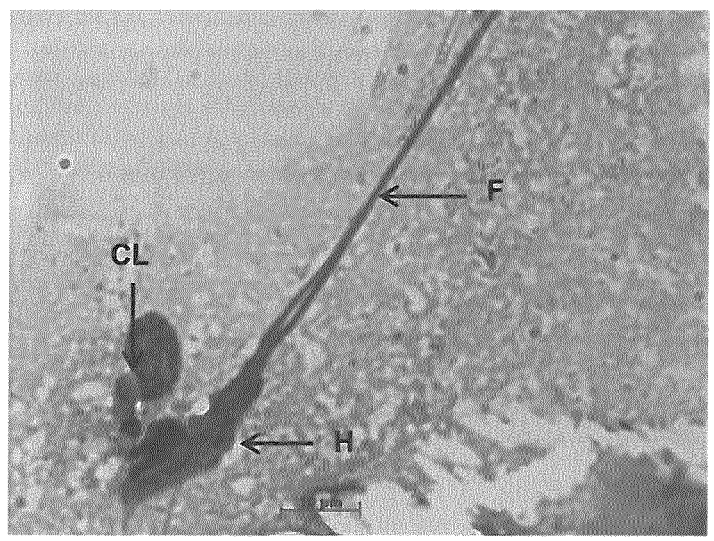

FIG. 7 shows an isolated spermatozoon (SZ) (step 19 of spermiogenesis). At a higher magnification (FIG. 8) it was observed the spermatozoon head (H), the cytoplasmic lobe (CL) and the flagellum (F) of the SZ.

These results show that the process according to the invention enables to carry out spermatogenesis from a germinal tissue, i.e. from spermatogonia to elongated spermatids or spermatozoa.

Results on 1.5-Year-Old Cynomolgus Monkeys

By analogy with the boys who have only spermatogonia in their testes, seminiferous tubules of two 1.5 year-old cynomolgus monkeys were cultured. Indeed, 1.5 year-old monkeys have only spermatogonia in their testes. After 54 days of culture, cells were obtained after spreading the crushed cultured seminiferous tubules.

Figure 11:
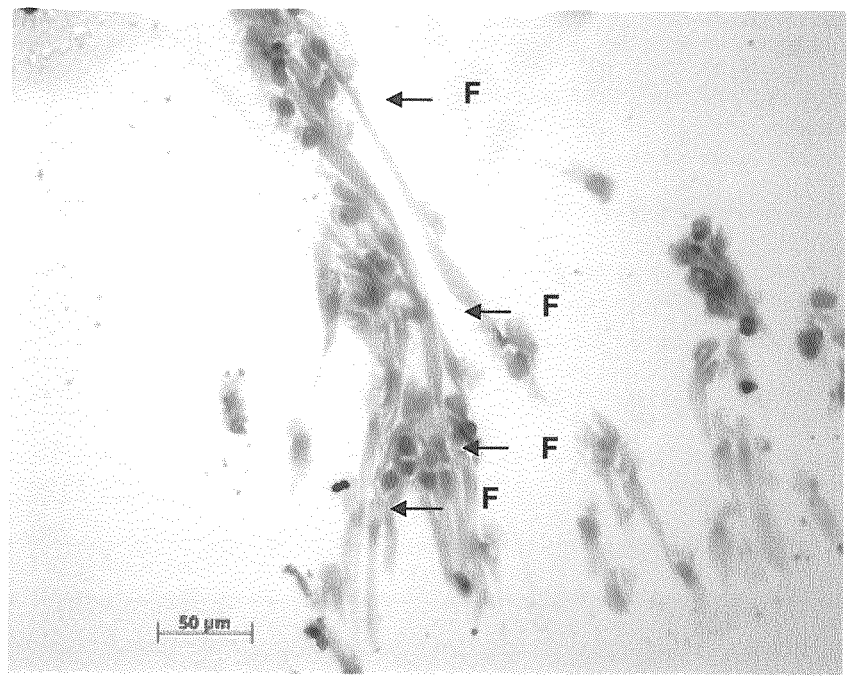
FIGS. 11, 12 and 13 represent germ cells of 1.5 year-old cynomologus monkeys after 54 days of culture.

FIG. 11, shows the sperm flagella (F).

Figure 12:
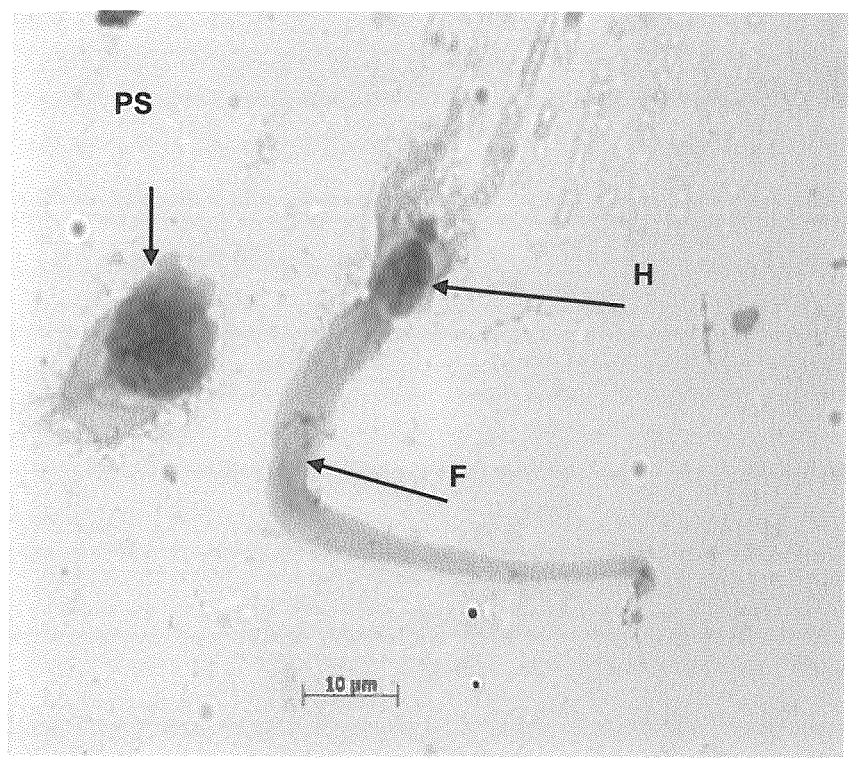

FIG. 12 shows the head (H) and the flagellum (F) of an ES at a higher magnification. A Pachytene spermatocyte (PS) is besides the ES.

Figure 13:
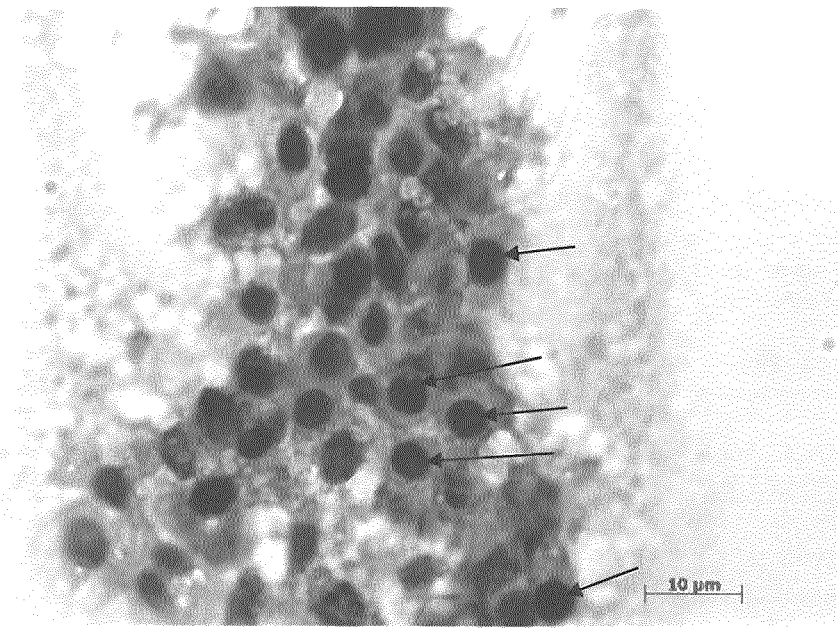

FIG. 13: The presence of young spermatocytes (shown by the arrows) indicates that a new wave of meiotic germ cells was ready to differentiate into spermatozoa.

Results on a Transsexual Man

Seminiferous tubules of a transsexual man were cultured. After a hormonal treatment that inhibited his spermatogenesis, this man had only spermatogonia, scarce preleptotene spermatocytes and Sertoli cells in his seminiferous tubules. This patient is close to a young boy who has only spermatogonia in his testes.

After 34 days of culture, cells were obtained after spreading the crushed cultured seminiferous tubules.

Figure 14:
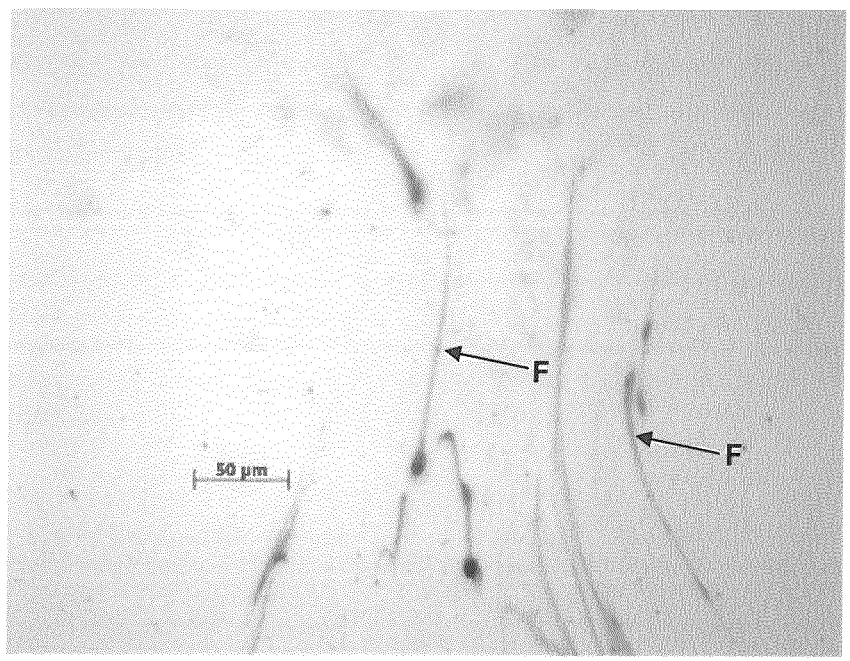
FIGS. 14 and 15 represent germ cells of transsexual man after 34 days of culture.

FIG. 14 shows flagella (F) of spermatozoa (shown by the arrows).

Figure 15:
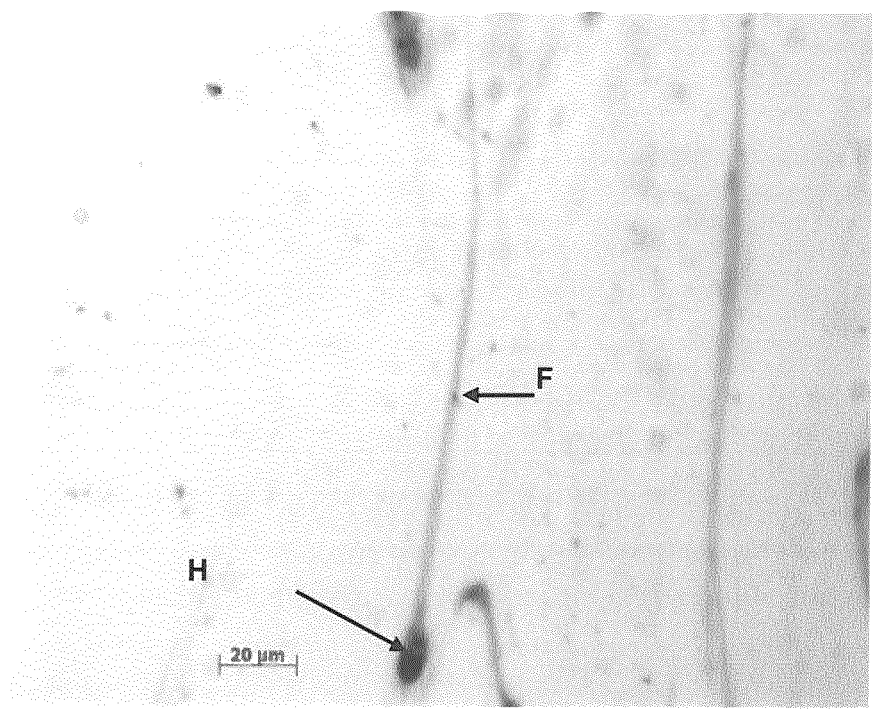

At a higher magnification, FIG. 15 shows the head (H) and the flagellum (F) of a spermatozoon.

The invention claimed is:

1. A method for in vitro spermatogenesis from male testicular tissue comprising:
   (a) conducting maturation of testicular tissue in a bioreactor which is made of a biomaterial and comprises at least one cavity wherein the testicular tissue is confined, said bioreactor being placed in or in the contact of a culture medium until elongated spermatids and/or spermatozoa are produced; and
   (b) recovering said elongated spermatids and/or spermatozoa,
   wherein said cavity is closed during the maturation process,
   wherein the bioreactor has a permeability that enables sufficient gas exchange and metabolite circulation between the culture medium and the cavity, and the biomaterial being a hydrogel that enables air, carbon dioxide, and the elements of the culture medium into which the bioreactor is placed for maturation to diffuse through it; and
   wherein the testicular tissue comprises germ cells, Sertoli cells and peritubular cells, where the germ cells are in close association with Sertoli cells.

2. The method according to claim 1, wherein the testicular tissue comprises at least one seminiferous tubule or fragments of at least one seminiferous tubule.

3. The method according to claim 2, wherein the testicular tissue comprises fragments from 2 to 50, 3 to 40, 4 to 30, or 5 to 20 seminiferous tubules.

4. The method according to claim 2, wherein the tubules and/or fragments are obtained through mechanical separation or enzymatic separation of seminiferous tubules.

5. The method according to claim 2, wherein the fragments of seminiferous tubules have a length between about 1 mm and about 5 mm.

6. The method according to claim 1, wherein the testicular tissue further comprises Leydig cells.

7. The method according to claim 1, wherein cells selected from the group consisting of germ cells, Sertoli cells, peritubular cells and mixtures thereof, are added to the testicular tissue.

8. The method according to claim 1, wherein the volume of the cavity or the volume of testicular tissue is from about 1 to about 100 mm$^3$, from about 0.5 to about 150 mm$^3$, or from about 1 to about 30 mm$^3$.

9. The method according to claim 1, wherein the testicular tissue is obtained from a subject selected from the group consisting of:
- a healthy prepubertal or postpubertal patient about to undergo a gonado-toxic treatment or surgery;
- a postpubertal patient who does not produce spermatozoa due to genetic or acquired non-obstrusive azoospermia, bilateral chryptorchidism during childhood or severe sickle cell disease;
- a prepubertal patient having bilateral chryptorchidism or severe sickle cell disease;
- endangered species;
- a horse, a camel, a dromedary or a pet; and
- livestock.

10. The method according to claim 1, wherein the biomaterial comprises collagen.

11. The method according to claim 1, wherein the biomaterial comprises a natural polysaccharide selected from the group consisting of chitosan, hyaluronic acid, alginate, pectin and a modified natural polysaccharide, and wherein said natural polysaccharide is used alone or in a mixture.

12. The method according to claim 1, further comprising:
i) providing a sample of testicular tissue comprising germ cells, Sertoli cells and peritubular cells, where the germ cells are in close association with Sertoli cells;
ii) providing a bioreactor which is made of a biomaterial and comprises at least one cavity, said bioreactor having a permeability that enables sufficient gas exchanges and metabolite circulation between the culture medium and the cavity comprising the testicular tissue, and the biomaterial being a hydrogel that enables air, carbon dioxide, and the elements of the culture medium into which the bioreactor is placed for maturation to diffuse through it;
iii) introducing said testicular tissue into the at least one cavity of said bioreactor and sealing the bioreactor; and
iv) placing said bioreactor containing said testicular tissue in a tank comprising a culture medium.

13. The method according to claim 1, wherein the bioreactor is formed around the testicular tissue during the formation of the bioreactor.

14. The method according to claim 1, wherein the bioreactor is a hollow fiber of a biomaterial comprising a channel wherein the testicular tissue is confined.

15. The method according to claim 1 wherein:
the culture medium comprises a material selected from the group consisting of growth factors, hormones, testosterone, vitamins, antibiotics, metabolites, and mixtures thereof
the culture medium comprises a material selected from the group consisting of growth factors, hormones, vitamins, antibiotics, metabolites, and mixtures thereof.

16. The method according to claim 1 wherein:
the culture medium comprises a material selected from the group consisting of growth factors, hormones, vitamins, antibiotics, metabolites, and mixtures thereof.

17. The method according to claim 1, wherein the thickness of the biomaterial is from about 0.1 to 10 mm.

18. The method according to claim 1, wherein testosterone is added in the culture medium during the course of the process.

19. The method according to claim 1, wherein the biomaterial is chitosan.

20. The method according to claim 1, wherein the bioreactor is a hollow fiber of chitosan comprising a channel wherein the testicular tissue is confined.

21. Process of in vitro fertilization comprising:
a) preparing of elongated spermatids and/or spermatozoa according to the process of claim 1; or providing elongated spermatids and/or spermatozoa by the process according to claim 1; and
b) fertilizing of an oocyte with the elongated spermatids and/or spermatozoa obtained.

* * * * *